(12) United States Patent
Al Ahmad et al.

(10) Patent No.: US 10,416,066 B2
(45) Date of Patent: Sep. 17, 2019

(54) METHOD OF CHARACTERIZATION OF EXOSOMES

(71) Applicant: United Arab Emirates University C/o Mohamed Al Hemairy m.hussien@uaeu.ac.ae;ip@uaeu.ac.ae, Al Ain (AE)

(72) Inventors: Mahmoud Al Ahmad, Al Ain (AE); Gulfaraz Khan, Al Ain (AE)

(73) Assignee: UNITED ARAB EMIRATES UNIVERSITY (AE)

( * ) Notice: Subject to any disclaimer, the term of this patent is extended or adjusted under 35 U.S.C. 154(b) by 204 days.

(21) Appl. No.: 15/703,216

(22) Filed: Sep. 13, 2017

(65) Prior Publication Data

US 2019/0078993 A1    Mar. 14, 2019

(51) Int. Cl.
| | |
|---|---|
| *G01N 15/10* | (2006.01) |
| *C12Q 1/04* | (2006.01) |
| *G01N 27/22* | (2006.01) |
| *G01N 33/487* | (2006.01) |
| *G01N 15/06* | (2006.01) |
| *G01N 15/00* | (2006.01) |

(52) U.S. Cl.
CPC ........... *G01N 15/1031* (2013.01); *C12Q 1/04* (2013.01); *G01N 15/0656* (2013.01); *G01N 27/221* (2013.01); *G01N 33/487* (2013.01); *G01N 33/48707* (2013.01); *G01N 2015/0038* (2013.01); *G01N 2015/0053* (2013.01); *G01N 2015/0065* (2013.01); *G01N 2015/1006* (2013.01)

(58) Field of Classification Search
CPC .................................................. G01N 15/1031
See application file for complete search history.

(56) References Cited

PUBLICATIONS

Tu, M., Wei, F., Yang, J., Wong, D. Detection of Exosomal Biomarker by Electric Field-induced Release and Measurement (EFIRM). J. Vis. Exp. (95), e52439, doi:10.3791/52439 (2015). (Year: 2015).*
Al-Ahmad et al. Sci Rep. 2016; 6: 34016. pp. 1-9. Published online Sep. 28, 1016. doi: 10.1038/srep34016 (Year: 2016).*

* cited by examiner

*Primary Examiner* — Scott Long
(74) *Attorney, Agent, or Firm* — Hayes Soloway PC

(57) ABSTRACT

The present invention discloses a method to electrically detect exosomes in a suspension medium, and identify whether the exosomes were released from diseased or healthy cells. The core principle of the method is that, when exosomes originating from diseased or healthy cells are polarized electrically, measurements can be conducted to identify unique and specific electrical capacitance signature, which can be used to characterize the exosomes and identify the cell types they originated from.

14 Claims, 1 Drawing Sheet

METHOD OF CHARACTERIZATION OF EXOSOMES

BACKGROUND

Field of Invention

The present invention relates to a method of electrical detection and characterization of exosomes, more particularly the present invention relates to a method of electrical identification and characterization of exosomes released from different cell types.

Description of Related Art

Exosomes are cell-derived vesicles that are released from and are present in most cell types. Exosomes can be released by varying types of cells into body fluids, including blood, urine, and also culture mediums of cell cultures. They are nano-sized particles, which are lipid-encapsulated, that is, they are vesicular bodies composed of lipid bilayer and contain proteins, nucleic acids and other constituents. Exosomes can potentially be used for prognosis, for therapy, and as biomarkers for health and disease, therefore there has been a growing interest in the clinical applications of exosomes.

The contribution to clinical applications is largely because exosomes contain RNA, proteins, lipids and metabolites that are reflective of the cell type from which the exosomes originated. Due to the multitude of information which can be derived from the materials contained in exosomes, and thereby the cell type of origin, there is an increased focus in the development of identification, quantification, and characterization techniques relating to exosomes.

The currently known conventional techniques used for exosome detection are labor-intensive, complex, costly and not time efficient. Common techniques usually incorporate a two-step procedure, wherein first the exosomes are extracted or isolated from body fluids and second detection of specific exosome biomarkers that are associated with a variety of diseases is conducted. The bio-recognition technologies and quantification depends on the biomolecules associated with the exosomes.

The conventional methods for isolating exosomes from body fluids are based on ultracentrifugation or precipitation. Multiple steps of ultra-centrifugation can be used to isolate vesicles of size typical of exosomes. However, further confirmation using bio-imaging or molecular biology techniques is usually necessary to confirm that the isolated vesicles are exosomes. Recently, other methodologies have been developed, including precipitation combined with centrifugation. These technologies are not only based on specificity but are also time consuming and may take from several hours to days to perform. Also, the bio-recognition methods require the addition of stabilization reagents along with exosome releasing agents, which can make the process complicated and introduce interference that could lead to errors.

Rapid and reliable methods of isolating and characterizing exosomes are of increased importance, due to the role which exosomes have been found to play in disease diagnosis. The currently available methods for characterizing exosomes can be classified into two categories: (1) biophysical and (2) molecular-based characterizations. Biophysical techniques include Raman spectroscopy, dynamic light scattering, scanning electron microscopy (SEM) and atomic force microscopy (AFM). Whereas, the molecular-based techniques include flow cytometry, transmission electron microscopy (TEM) and nanotechnology-dependent exosome characterization methodologies.

These techniques have various drawbacks including the use of sophisticated equipment, the limitation on the size of particles that can be detected, and the amount of time required for each technique to be conducted.

Hence, to overcome the current drawbacks and challenges in performing exosomal analysis, it is necessary to develop a method of label-free detection and characterization of exosomes which is less complex, is more accurate and is considerably less time consuming.

It is therefore an object of the present invention to provide a method for detection and characterization of exosomes which does not rely on bio-imagining or complex molecular biology techniques.

It is a further objective of the present invention to provide a method for detection and characterization of exosomes that is label-free.

It is a further objective of the present invention to provide a method for detection and characterization of exosomes that is rapid, and less complex than currently known methods.

SUMMARY OF INVENTION

It is an object of the present invention to distinguish exosomes that are released from diseased cells, such as virally-infected or cancerous cells, from those that are released by healthy cells. The present invention discloses a method to electrically detect exosomes in a suspension medium, and identify whether the exosomes were released from diseased or healthy cells. The core principle of the method is that, when exosomes originating from diseased or healthy cells are polarized electrically, measurements can be conducted to identify unique and specific electrical capacitance signature, which in turn can be used to for laboratory diagnosis of various diseases, ranging from cancer to infections. The method can be used as rapid, reproducible and label-free electrical based technique for the detection of exosomes released in body fluids, such as blood, urine and milk in different conditions.

In accordance with one embodiment of the present invention, a method of characterization of exosomes, is disclosed, wherein the method comprises the following steps:
  isolating exosomes from cell cultures;
  preparing a suspension containing the isolated exosomes;
  subjecting the suspension to an electrical field;
  inducing an electrical charge in the exosomes;
  determining an electrical charging profile based on the charging rate of the suspension containing the isolated exosomes;
  measuring capacitance as a function of voltage to create a capacitance voltage profile;
  identifying characteristics of the exosomes based on the capacitance voltage profile.

According to a first step of the presently disclosed method, the exosomes are isolated from their respective cell cultures. Various currently know separation/extraction methods to those skilled in the art, can be utilized for the isolation step. For example, the exosomes can be isolated through the use of differential ultracentrifugation, which extracts the exosomes from the respective cell line.

According to a second step of the presently disclosed method, the isolated exosomes are then placed in a suspension, using a suspension medium.

The suspension containing the exosomes is then subjected to an electrical field. An electrical field is propagated throughout the suspension medium, and the exosomes are polarized and an electrical charge is induced in the exosomes.

Measurements are then conducted for determining an electrical charging profile based on the charging rate of the suspension containing the isolated exosomes. The electrical charging profile consists of voltage measurements as a function of time.

In accordance with another step of the present method, measurements are conducted to determine the capacitance as function of voltage to create a capacitance voltage profile for the suspension containing the isolated exosomes. Capacitance is measured as voltage is applied to the suspension. This step allows for the creating of a capacitance as a function of voltage) which is uniquely attributable to the exosome content within the suspension. In practice, this capacitance voltage profile can be used as an identifying "signature" specific to the particular exosomes which were released from their respective cell types.

Once the capacitance voltage profile is created, the profile can be used to identify characteristics of the exosomes, such as identifying the cell type the exosomes originate from.

In one embodiment of the present invention, identifying the characteristics includes using the capacitance voltage profile to determine whether the exosomes were released from virally infected cells, cancerous cells or healthy cells. Furthermore, the specific type of virus infected cell, or cancerous cell can be identified.

In one embodiment of the present invention, the exosome characterization method further comprises a step of conducting the above described method steps for creating a capacitance voltage profile for a control suspension, which only includes the suspension medium and is devoid of any exosome content. This is for purposes of a comparison reference with the capacitance voltage profiles, of suspension mediums containing the exosomes.

In practice, for the identification of the cell type origin of particular exosomes, it is envisioned that a database is created which contains the various unique capacitance voltage profiles references, i.e. reference "signatures", for exosomes which were derived from various types of cells, including diseased and healthy cells. The database can be used to rapidly conduct medical diagnostics and identify newly tested exosome samples and match the capacitance voltage profiles, with existing profiles within the database, so that the originator cell type and hence the disease can be identified. This can for example be cells from various types of viral infections, various types of cancer cells, cells from other known diseases, or healthy cells.

In one embodiment, the originator cell type is an Epstein-Barr virus infected cell.

In another embodiment, the originator cell type is a cancerous cell.

In an additional embodiment, the cell types are mammalian cells.

BRIEF DESCRIPTION OF THE FIGURES

The accompanying figures are included to provide a further understanding of the invention, and are incorporated in and constitute a part of this specification. The figures illustrate embodiments of the invention and, together with the description, serve to explain the principles of the invention.

In the figures.

DETAILED DESCRIPTION

Figure 1A:
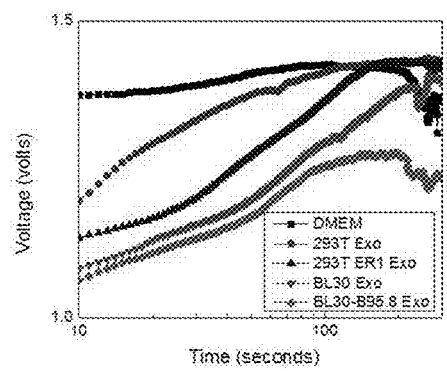
FIG. 1(a) illustrates an exemplary charging profile of various suspension mediums in accordance with exemplary embodiments of the present invention.

In the following Detailed Description, reference is made to the accompanying drawings, which form a part hereof, and in which is shown by way of illustration specific embodiments in which the invention may be practiced. Wherever possible, the same reference numbers are used in the drawings and the description to refer to the same or like parts. It is to be understood that other embodiments may be utilized and structural or logical changes may be made without departing from the scope of the present invention. The following detailed description, therefore, is not to be taken in a limiting sense, and the scope of the present invention is defined by the appended claims.

An exosome is comprised of a lipid bilayer membrane which contains proteins, nucleic acids and other components, which can be polarized when subjected to an electrical field. The present invention utilises this principle for a novel technique that is based on measuring the electrical capacitance and voltage signatures of exosome suspensions. When an exosome suspension is subjected to an electrical field, the exosome particles will get charged. The amount of this charge will depend on their intrinsic physical properties, mainly the dielectric constant. The propagation of the electrical field polarizes the exosome particles through an induced charging effect. On the other hand, the presence of exosomes will alter the propagated fields in magnitude and phase, thus enabling their electrical detection.

A single exosome particle can be modelled as an electrical dipole, which has two pairs of electrical charges of equal magnitude but opposite sign, separated by a distance less than its diameter. Furthermore, the strength of this polarization depends upon the composition and content of the exosome along with its interaction with the polarity of the suspension medium.

When a nano-sized organic particle, such as an exosome, becomes more polarized than its suspension medium, the net induced dipole on that particle will be aligned with the applied electric field. In this scenario the particle could be modelled as a conductive body. Alternatively, if the particle is less polarized than its suspension medium, the net induced dipole on that particle will be aligned counter to the applied electric filed, in which case the particle can be modelled as an insulator body. If both particle and suspension medium have the same polarization strength, the electrical field will not be disturbed, and therefore nothing will be detected.

Presently it is difficult to distinguish exosomes that are released from viral-infected or cancerous cells, from those that are released by healthy cells. The present invention discloses a method to electrically detect exosomes in a suspension medium, and identify whether the exosomes were released from diseased or healthy cells. The core principle of the method is that, when exosomes originating from diseased or healthy cells are polarized electrically, measurements can be conducted to identify unique and specific electrical capacitance signature, which can be used to characterize the exosomes and identify the cell types they originated from. The method can be used as rapid, reproducible and label-free electrical based technique for the detection of exosomes released from different cell types.

In accordance with one embodiment of the present invention, a method of characterization of exosomes, is disclosed, wherein the method comprises the following steps:
  isolating exosomes from cell cultures;
  preparing a suspension containing the isolated exosomes;
  subjecting the suspension to an electrical field;
  inducing an electrical charge in the exosomes;
  determining an electrical charging profile based on the charging rate of the suspension containing the isolated exosomes;
  measuring capacitance as a function of voltage to create a capacitance voltage profile;
  identifying characteristics of the exosomes based on the capacitance voltage profile.

According to a first step of the presently disclosed method, the exosomes are isolated from their respective cell cultures. Various currently know separation/extraction methods to those skilled in the art, can be utilized for the isolation step. For example, the exosomes can be isolated through the use of differential ultracentrifugation, which extracts the exosomes from the respective cell line. Although, this is merely exemplary, and other known methods of extraction and isolation of exosomes can be utilized.

According to a second step of the presently disclosed method, the isolated exosomes are then placed in a suspension, using a suspension medium. The medium to be used for example can be DMEM, or any other suitable cell culture medium currently known in the field.

The suspension containing the exosomes is then subjected to an electrical field. During this step, the suspension is placed in a sample chamber of a two electrode based structure. A voltage source is coupled to the two electrode based structure and a constant current is provided. An electrical field is propagated throughout the suspension medium, and the exosomes are polarized and an electrical charge is induced in the exosomes. Reference is made to the two-electrode based structure disclosed in applicant's own patent publication WO 2016/030713, which is applicable to the present invention, and which describes the structure and its functionality in detail, and is hereby incorporated by reference.

Measurements are then conducted for determining an electrical charging profile based on the charging rate of the suspension containing the isolated exosomes. During this, the suspension can for example be subjected to a constant capacity of 1 mA-h at a constant current of 0.05 mA for a brief time, for example 5-15 minutes. The electrical charging profile consists of voltage measurements as a function of time, as will be explained in more detail in relation to FIG. 1(a).

In accordance with another step of the present method, measurements are conducted to determine the capacitance as function of voltage at a specific frequency to create a capacitance voltage profile for the suspension containing the isolated exosomes. Capacitance is measured as voltage is applied to the suspension. The voltage for example can be varied from −0.5 volt to 0.5 volt, with a voltage step of 0.05 volts, at a frequency of 10 Hz. This step allows for the creating of a capacitance as a function of voltage (also referred to as a capacitance voltage profile, throughout this text) which is uniquely attributable to the exosome content within the suspension. In practice, this capacitance voltage profile can be used as an identifying "signature" specific to the particular exosomes which were released from their respective cell types. This signature is also created for the suspension medium without the exosomes, so that the parameters measured in the medium without the exosomes present can be de-embedded from the parameters obtained when the exosomes are present. This way the signature characteristics of various exosomes can be obtained and the suspension medium is already accounted for.

Once the capacitance voltage profile is created, the profile can be used to identify characteristics of the exosomes. Identifying the characteristics for example includes identifying the cell type the exosomes originate from.

In one embodiment of the present invention, identifying the characteristics includes using the capacitance voltage profile to determine whether the exosomes were released from virally infected cells, cancerous cells or healthy cells. Furthermore, the specific type of virus infected cell, or cancerous cell can be identified, as will be described in further detailed in relation to FIG. 1(b). Detailed discussion is provided below for example, where the present method is used to electrically identify cell types, such as human embryonic kidney cells, and Burkitt's lymphoma cells cancer cells. The healthy and virally infected cell lines were studied with the present method, and both can be identified separately due to their unique capacitance voltage profile, i.e. their unique electrical signature.

In one embodiment of the present invention, the exosome characterization method further comprises a step of conducting the above described method steps for creating a capacitance voltage profile for a control suspension, which only includes the suspension medium and is devoid of any exosome content. This is for purposes of a comparison reference with the capacitance voltage profiles, of suspension mediums containing the exosomes.

In practice, for the identification of the cell type origin of particular exosomes, it is envisioned that a database is created which contains the various unique capacitance voltage profiles references, i.e. reference "signatures", for exosomes which were derived from various types of cells, including diseased and healthy cells. The database can be used to rapidly conduct medical diagnostics and identify newly tested exosome samples and match the capacitance voltage profiles, with existing profiles within the database, so that the originator cell type can be identified. This can for example be cells from various types of virally infected cells, various types of cancer cells, cells from other known diseases, or healthy cells.

In one embodiment, the originator cell type is an Epstein-Barr virus infected cell.

In another embodiment, the originator cell type is a cancerous cell.

In an additional embodiment, the cell types are mammalian cells.

The following discussion provides detailed examples of the above described characterization method, which resulted from experiments conducted on various cell types in accordance with the principles of the present invention. The following discussion is exemplary, and should not be interpreted as limiting the scope of the present invention in any way. Although for purposes of the following examples, Epstein Barr infected cells were studied, the method is reliable and reproducible for a myriad of other known virus types, the list of which is too extensive to reproduce here.

Exosomes from Epstein-Barr virus (EBV) infected and non-infected cells were tested in accordance with the method of the present invention. Exosomes were isolated from culture supernatants of four different cell lines, namely: 293T cells (human embryonic kidney cells); 293T ER1 cells (293T cells transfected with Epstein-Barr virus encoding RNA1, EBER1); BL30 (an EBV-negative Burkitt's lymphoma cell line) and BL30-B95.8 (an EBV-infected derivative of BL30).

All the cell lines were grown according to their specific required conditions and their respective exosomes isolated from culture supernatants using gradient ultracentrifugation. Purified exosomes were examined by transmission electron microscopy (TEM). Nanosize vesicles ranging from 50-150 µM with morphology typical of exosomes were identified. Western blotting for the exosomal markers CD63 and flotillin confirmed that these nano-vesicles seen under electron microscopy were exosomes. However, based on the morphology, exosomes from infected and non-infected cells could not be distinguished from one another.

To conduct the charging and capacitance voltage measurements, the exosome containing suspensions were individually loaded inside an open-ended coaxial capacitance structure (this structure is similar in construction and function to the device described in applicant's own patent application WO 2016/030713, which is incorporated herein by reference) and the measurement of data was conducted using a Gamry 3000 equipment which has a wide range of electrical measurement capabilities. A control suspension medium (DMEM) devoid of exosomes was also tested, for comparison purposes.

FIG. 1(a) shows the electrical charging profiles of the exosome suspensions along with the control suspension medium (DMEM) when subjected to constant capacity of 1 mA-h with constant currents of 0.5 mA for 5 minutes.

As can be seen in FIG. 1(a) the control suspension medium (DMEM) charging level is higher than the exosome containing suspensions. The charging profile for the DMEM exhibits linear response with respect to a constant charging rate, while the exosome containing suspensions exhibit lower charging rates as the exosomes take some time to get fully charged.

The lowest charging rates were noted with exosomes from EBV infected cells (BL30-B95.8). The uninfected derivative of the same cell line (BL30) shows a clearly higher charging rate. These findings imply that the exosomes released from the viral infected and uninfected cells of exactly the same type, contain different contents and thus have different electrical signatures.

Figure 1B:
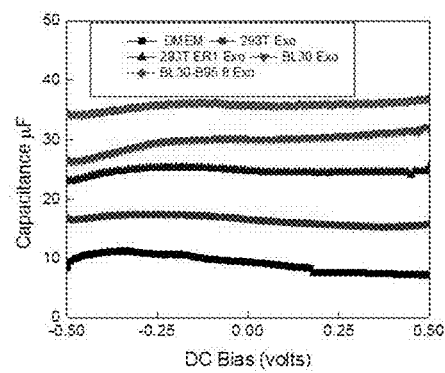
FIG. 1(b) illustrates an exemplary capacitance as a function of voltage profile of various suspension mediums in accordance with exemplary embodiments of the present invention.

FIG. 1(b) shows the capacitance voltage measurements which depict a smooth capacitance-voltage dependency. As expected, the suspension media (DMEM) without exosomes showed the lowest capacitance values. Whereas the exosome containing suspensions clearly show higher capacitance. Furthermore, exosomes from BL30 cells (non-infected) and its infected counterpart BL30-B95.8, had distinct capacitances. Exosomes from the infected cells had higher capacitance compared to exosomes from the non-infected counterpart cell line. Interestingly, exosomes from 293T cells and their EBER1 transfected counterparts (293T-ER1) also had distinct capacitances; exosomes from transfected cells had higher capacitance compared to exosomes from the non-transfected cells. These differences strongly depend on the composition of the exosome components which plays an important role in polarization and ability of the exosomes to hold charges.

The effect of dilution was also investigated with respect to the electrical properties of the exosome containing suspensions. The BL30 exosome stock was diluted by a factor of 2, 10 and 100 using the DMEM suspension medium. The capacitance voltage dependency at 10 Hz frequency was then measured. The data showed that the more concentrated the exosome suspension, the higher the observed effective capacitance values.

While selected embodiments have been selected to be illustrated of the present invention, and specific examples have been described herein, it will be obvious to those skilled in the art that various changes and modifications may be aimed to cover in the appended claims. It will, therefore, be understood by those skilled in the art that the particular embodiments of the invention presented here are by way of illustration only, and are not meant to be in any way restrictive; therefore, numerous changes and modifications may be made, and the full use of equivalents resorted to, without departing from the spirit or scope of the invention as outlined in the appended claims.

The invention claimed is:

1. A method of characterization of exosomes, the method comprising:
    isolating said exosomes from cell cultures;
    preparing a suspension containing the isolated exosomes;
    subjecting said suspension to an electrical field;
    inducing an electrical charge within the exosomes;
    determining an electrical charging profile based on the charging rate of the suspension containing the isolated exosomes;
    measuring capacitance as a function of voltage to create a capacitance voltage profile;
    identifying characteristics of the exosomes based on the capacitance voltage profile.

2. The method of claim 1, wherein identifying characteristics of the exosomes comprises identifying whether the exosomes originate from a diseased cells or healthy cells.

3. The method of claim 1, wherein identifying characteristics of the exosomes comprises identifying the cell type the exosomes originate from.

4. The method of claim 3, wherein the said cell type comprises virally infected cells, cancerous cells or healthy cells.

5. The method of claim 1, wherein the step of subjecting said suspensions to an electrical field occurs in a two electrode based structure.

6. The method of claim 1, wherein said suspensions are subjected to an electrical field at constant capacity and constant current.

7. The method of claim 6, wherein the constant capacity is about 1 mA/h, and the constant current is about 0.5 mA.

8. The method of claim 1, wherein the step of measuring capacitance as a function of voltage is conducted at a DC bias voltage between −0.5 volts to 0.5 volts, with a voltage step of 0.05, at a frequency of 10 Hz.

9. The method of claim 1, further comprising creating a capacitance voltage profile for a control suspension, for use as a comparison reference.

10. The method of claim 3, wherein the cell type is a mammalian cell.

11. The method of claim 3, wherein the cell type is an Epstein-Barr infected cell.

12. The method of claim 3, wherein the cell type is Burkitt's lymphoma cell type.

13. The method of claim 1, wherein after the isolation steps, the isolated exosomes are visualized and confirmed using Transmission Electron Microscopy.

14. The method of claim 1, further comprising creating a capacitance voltage profile for varying dilutions of exosome containing suspensions.

* * * * *